United States Patent [19]

Perez et al.

[11] Patent Number: 4,955,087
[45] Date of Patent: Sep. 11, 1990

[54] COMBINED VISOR AND SUNGLASSES ASSEMBLY

[76] Inventors: Richard Perez, 11201 SW. 55 St., Miramar, Fla. 33025; Jose F. Deida, 381 W. 14 St., Hialeah, Fla. 33010

[21] Appl. No.: 244,838

[22] Filed: Sep. 15, 1988

[51] Int. Cl.⁵ .............................................. A61F 9/00
[52] U.S. Cl. ............................................. 2/12; 2/9;
2/426; 2/443; 2/447; 2/452; 2/453
[58] Field of Search ................. 2/9, 15, 426, 424, 427, 2/434, 453, 443, 12, 451, 452, 447

[56] References Cited

U.S. PATENT DOCUMENTS

| | | | |
|---|---|---|---|
| 1,455,025 | 5/1923 | Kern-Jenny et al. | 2/15 X |
| 2,655,657 | 10/1953 | Lueders | 2/453 X |
| 2,731,637 | 1/1956 | Kaplan et al. | 2/9 |
| 2,881,443 | 4/1959 | Barker, Jr. | 2/9 |
| 3,016,543 | 1/1962 | Lindblom | 2/9 |
| 3,133,982 | 5/1964 | Janz | 2/426 X |
| 3,896,496 | 7/1975 | Leblanc et al. | 2/443 X |
| 4,455,689 | 6/1984 | Boyer | 2/434 |
| 4,811,430 | 3/1989 | Janusz | 2/452 |
| 4,885,808 | 12/1989 | Carpenter | 2/452 |
| 4,901,374 | 2/1990 | Vander Woude | 2/452 X |

FOREIGN PATENT DOCUMENTS 2918635  11/1980  Fed. Rep. of Germany .......... 2/424

Primary Examiner—Werner H. Schroeder
Assistant Examiner—Jeanette E. Chapman
Attorney, Agent, or Firm—Malloy, Downey & Malloy

[57] ABSTRACT

A combination sun visor and sunglasses assembly including a mounting structure designed to surround the head of the wearer similar to a headband wherein the lens structure or viewing portion of the sunglasses are positionable between an overlying, normally viewing position relative to the eyes of the wearer or an outwardly extending, shading position similar to an orientation of a visor structure in overhanging, shading position.

15 Claims, 2 Drawing Sheets

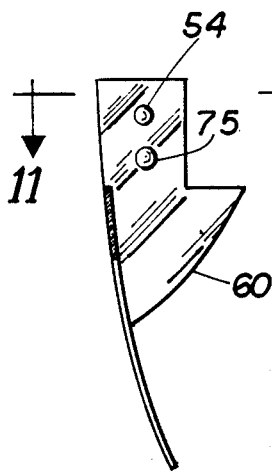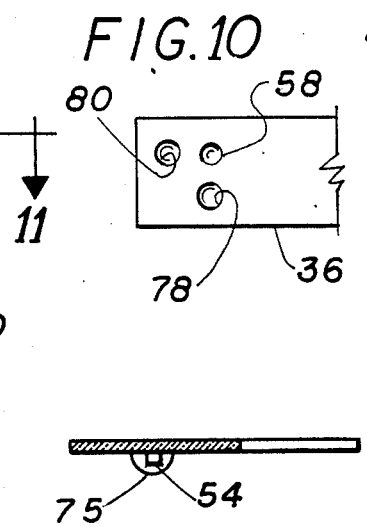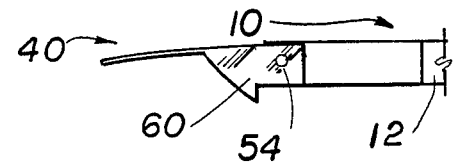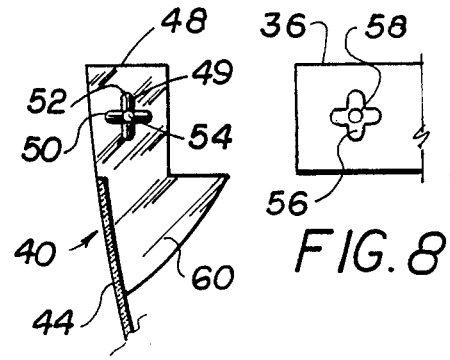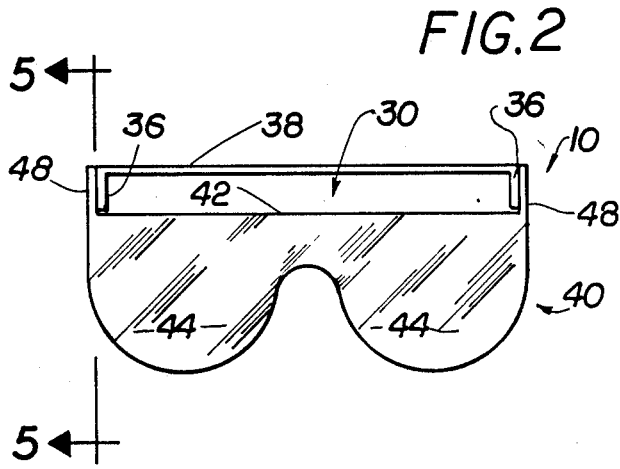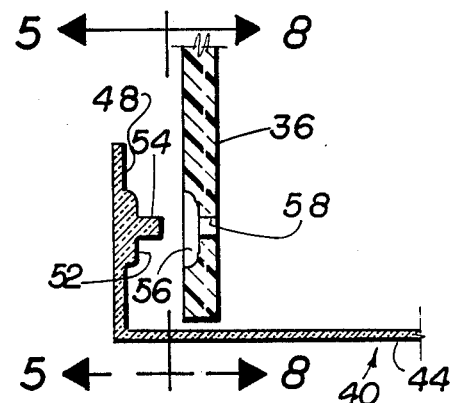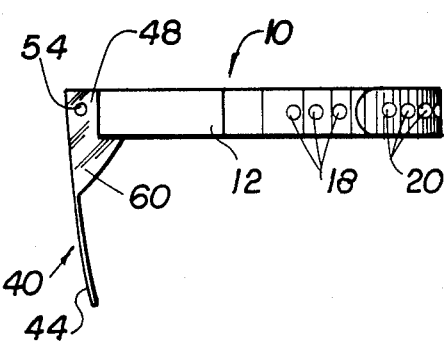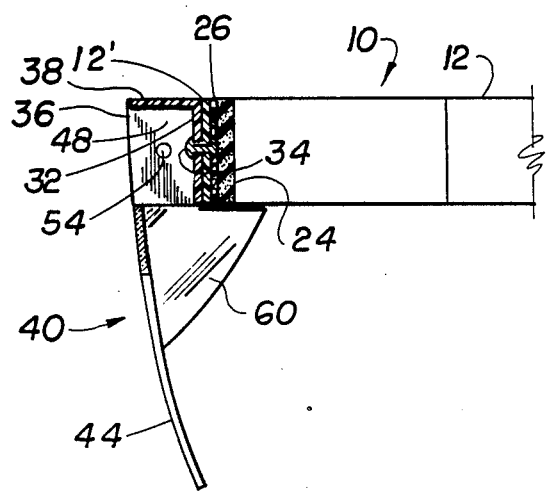

COMBINED VISOR AND SUNGLASSES ASSEMBLY

BACKGROUND OF THE INVENTION

1. Field of the Invention

This invention relates to an assembly to be worn about the head of a person and structured to include a darkened, transparent material lens structure functional as sunglasses but also positionable into an outwardly extending overhanging relation to the eyes of the wearer and out of the viewing path relative thereto so as to effectively function as a visor.

2. Description of the Prior Art

The prior art is of course replete with various types of sunglasses and/or shading devices structured to accomplish viewing by the wearer directly through darkened lens portions which effectively serve as sunglasses. Alternately the structure of the prior art device extends in an overhanging, outwardly extending relation to the eyes of the wearer and thereby serves as a shading or visor structure. Typically, prior art devices include attachment to the wearer through some type of support frame including an elongated temple portion set on the sides of the head and somehow connected in supported relation on or about the ears of the wearer. Also, it is typical for such structures to be depending from or supported on the bridge of the nose. While apparently operable or functional for their intended function, prior art devices of the type set forth in the following U.S. Patents are frequently not efficiently usable as both eyeglasses and visor structures.

For example, U.S. Pat. No. 2,616,082 to Creighton discloses a combination eye shade and sunglasses wherein temple-type structures 88 extend back along the temples of the head of the wearer similar to typical eyeglasses and wherein the lens portions thereof are supported on the bridge of the nose or substantially adjacent thereto in a generally conventional fashion. Mendelsohn, U.S. Pat. No. 2,582,554, and Hanford, U.S. Pat. No. 2,632,164, disclose generally similar structures. One problem associated with the structures disclosed in the aforementioned patents also relates to the method of properly positioning the shading or lens portion of the assembly in a preselected position. Typically, such devices used to position the assembly as intended are either over complicated, or inefficient and difficult to manipulate and/or attend to such positioning. The patents to Vivolo, U.S. Pat. No. 2,968,812; Muller, U.S. Pat. No. 3,212,102; and Hoffman, U.S. Pat. No. 3,295,143, all disclose a shading structure or glare shield utilizing some type of glare or sun shield or shading structure positionable at a preselected location relative to the eyes of the wearer of the assembly.

Prior art devices generally relating to the same subject matter but differing therefrom at least to some extent include the patent to Jean Jr., U.S. Pat. No. 4,616,367, disclosing a soft material headband with separate lens structures positionable into and out of overlying, viewing relation to the eyes of the wearer. Similarly, Daigle, U.S. Pat. No. 4,712,254, is directed towards the headband and eye piece combination also wherein the lens portions are completely hidden when not in use as sunglasses. Finally, Schmidthaler, U.S. Pat. No. 4,578,822, discloses a visor type article including a relatively rigid arcuate shaped band member and an adjustable elastic strap cooperative with the band member to encircle the wearer's head. The device incorporates the concept of a replaceable visor structure having marginal end portions adapted to be releaseably inserted into a slot in a proper and preferred location. This structure does not incorporate the visor being also used as sunglasses, however.

While the structures set forth in the above-noted patents are considered to be operable for their intended function, there is still a recognized need and room for improvement in a combined visor structure and sunglasses wherein the wearer thereof can selectively position proper darkened viewing lenses between two operable positions to accomplish both functions.

SUMMARY OF THE INVENTION

The present invention relates to an assembly which can be selectively worn either as sunglasses or as a visor structure. A mounting means used to secure the entire assembly in proper positioning about the head of the wearer comprises a headband type structure formed of a relatively flexible material preferably such as plastic so as to readily adapt itself to the configuration of the wearer's head. Further, some type of adjustment feature may be incorporated therein such that the length or more specifically the circumference size is adjustable to adapt to the size of any wearer's head.

A sweatband and/or combined moisture absorber and cushioning member may be removably mounted along a portion of the interior surface of the headband so as to add not only comfort but serve as a "sweatband" in order to remove excess moisture from the contacted surfaces on the wearer's head.

A bracket extends outwardly from a frontal portion of the headband in substantially overhanging relation to the face and/or eyes of the wearer. The bracket has a transverse dimension to extend substantially across the face and extends outwardly from the headband a sufficient distance to allow a depending support of a lens structure thereon. The lens structure thereby depends in a downwardly hanging and specifically overlying relation to the eyes of the wearer such that the path of viewing of the wearer passes directly through the lens structure. In order to accomplish proper protection of glare from reaching the eyes, the lens structure may be formed, at least in part, from a darkened and/or polarized, transparent material through which the wearer may readily view.

The lens structure is movably mounted and connected to the bracket structure by positioning means secured at opposite, correspondingly positioned ends of both the lens structure and the bracket structure such that the lens structure may be selectively positioned and removably maintained in either one of a viewing position or shading position. The shading position of the lens structure is defined by a substantially outwardly extending relation of the lens structure to the face of the wearer as well as the bracket and in overhanging but not overlying relation to the eyes of the wearer. When in the aforementioned shading position, the lens structure provides a shading of the eyes and face of the wearer similar to that accomplished by an outwardly extending rim of a hat or cap. Due to the specific structure, placement and relative dimensions of the various components comprising the positioning means, the lens structure may be easily positioned into either of the viewing or shading position and maintained in such position without a significant tendency of the lens structure to be inadvertently displaced therefrom.

In addition, the lens structure is specifically dimensioned and configured to be removed from any supported contact on the bridge of the nose or other portions of the face. To the contrary, the lens structure is supported entirely by the bracket structure whether the lens structure is disposed in either of the viewing or shading positions.

Other features of the lens structure include side visors which are disposed in somewhat transverse relation to the remaining viewing portion of the lens structure and extend substantially sideways in overlying relation to the corner or outer ends of the eyes in order to prevent glare or unwanted light from passing into contact with the eyes from this outside position.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which:

FIG. 2 is a front plan view of the assembly wherein a lens structure thereof is shown in a viewing position.

FIG. 3 is a side view of the embodiment of FIG. 2.

FIG. 4 is a side view in partial cut-away wherein the lens structure is shown in a shading position.

FIG. 5 is a detailed view in partial cut-away in section along line 5—5 of FIG. 2.

FIG. 6 is a detailed view in section and cut-away along line 6—6 of FIG. 1.

FIG. 7 is a sectional view in partial cut-away along line 7—7 of FIG. 1.

FIG. 8 is a detail view in partial cut-away showing a configuration of the embodiment of FIG. 6 and taken along line 8—8 thereof.

FIG. 9 is a detail view in partial section of yet another embodiment of the positioning means of the present invention.

FIG. 10 is a detail view in partial cut-away of cooperative components of the embodiment of FIG. 9.

FIG. 11 is an end view taken along line 11—11 of FIG. 9.

Like reference numerals refer to like parts throughout the several views of the drawings.

DETAILED DESCRIPTION OF THE PREFERRED EMBODIMENT

Figure 1:
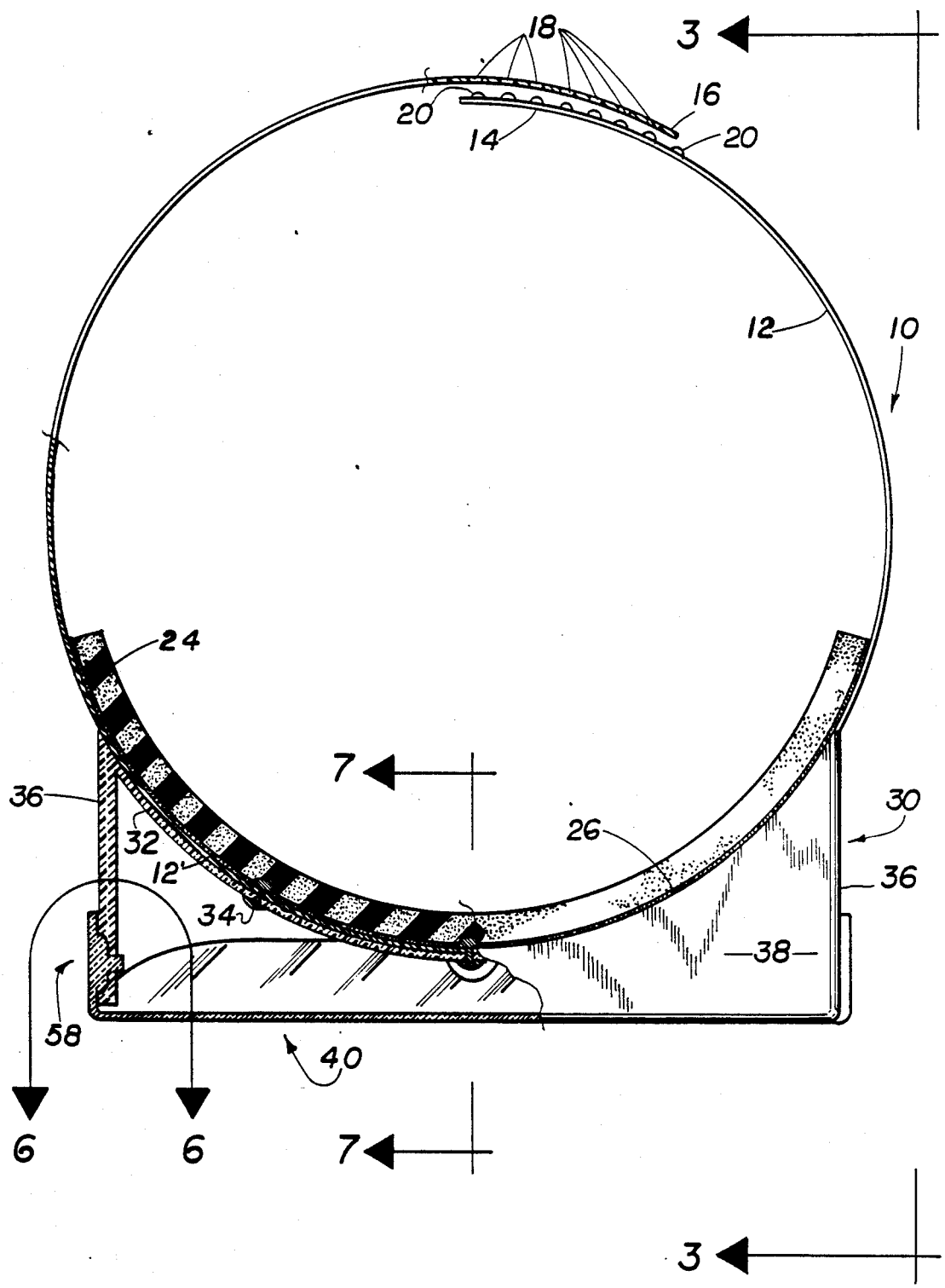
FIG. 1 is a top sectional view showing the relative cooperative positioning and interconnection of the components of the subject assembly.

As shown in FIGS. 1 through 7, the present invention is directed towards a combined sun visor and sunglasses assembly generally indicated as 10. The assembly includes a mounting means in the form of a headband 12 for securing the assembly about the head of the wearer. The headband 12 is formed from a somewhat flexible and adaptable material, such as plastic, and is of sufficient length to extend in completely surrounding relation about the head of the wearer. In the embodiment shown in FIG. 1, the headband 12 includes two opposite ends 14 and 16 which are separable but adjustably interconnected to one another by a plurality of cooperative apertures and outwardly extending teeth 18 and 20 respectively. Therefore, while the adjustable feature associated with the head band 12 is defined by the preferred and selected interconnection of the opposite ends 14 and 16. Any other adjustment means may be utilized and still be within the intended scope of the present invention.

Also in the embodiment of FIGS. 1 and 7, the headband 12 includes an elongated removably attached strip 24 formed of a soft, flexible and possibly resilient material which is also moisture absorbent. Accordingly, the elongated strip may define a "sweatband" extending along at least the frontal portion of the headband 12 as best shown in FIG. 1. The headband 12 may include any type of removable connection such as a hook and loop type fastener 26 commonly known and commercially available under the trademark "VELCRO." By virtue of the removable attachment of the strip 24, it may be easily removed and reattached in the preferred position shown in FIGS. 1 and 7 for purposes of replacement and/or washing. Therefore, a plurality of replacement bands 24 could be supplied with the assembly at the time of purchase or obtained independents thereof.

The assembly 10 of the present invention further comprises a bracket structure 30 including a substantially concave mounting strip 32 adapted to the configuration of the frontal portion of the headband 12 as at 12= (see FIGS. 1 and 7) and secured thereto such as by connectors such as staples or like connectors 34. In order to ensure that the wearer will not be subjected to any unnecessary discomfort, the elongated strip 24 or sweatband effectively covers the correspondingly positioned end of each of the connectors 34 so that such ends will not come into contact with the skin of the wearer. The bracket structure 30 includes two outwardly extending arms or support portions 36 having one end integrally or otherwise attached to the mounting strip 32 and the opposite end disposed and structured to removably support a lens structure generally indicated as 40 thereon. As best pictured in FIGS. 2 and 4, the bracket structure 30 also includes a top or cover member 38 extending along the length of the bracket structure and integrally secured or interconnected to the outwardly extending arms 36. As also shown in FIG. 2, the top or cover portion 38 of the bracket structure 30 is spaced from an upper peripheral edge 42 of the lens structure 40 in order to facilitate selective rotational movement of the lens structure relative to the bracket.

The lens structure 40 includes two lens portions or viewing portions 44 which, when positioned in the "viewing position," disclosed in FIGS. 2 and 3, are disposed in directly overlying relation to the eyes of the wearer such that the viewing path of the wearer is directly through the lenses or viewing portions 44 of the lens structure 40. Proper shading is provided by virtue of the formation of the lens structure 40 and particularly the lens portions 44 thereof from a darkened and/or polarized transparent material.

Further structural features associated with the lens structure 40 is its connection to a leading portion of the bracket 30. More specifically two oppositely disposed ends 48 of lens structure 40 are disposed in overlapping and/or confronting engagement with the exterior surfaces of the outwardly extending arms 36 of the bracket structure 30 as clearly shown in FIGS. 1, 2 and 5. These opposite ends 48 have a positioning means at least partially mounted thereon in the form of a first member projecting outwardly as at 49. This first member or portion of the positioning means is defined by two intersecting outwardly projecting arms 50 and 52 having a common substantially centrally located junction from which an outwardly extending finger projects as at 54 (see FIGS. 4 and 6). Similarly, the positioning means includes a receiving socket in the form of two transversely intersecting channels 56 wherein a centrally disposed aperture is formed at the junction of such channels 56 and is indicated as at 58 (see FIGS. 6 and 8). The transverse channels 56 are disposed, configured and dimensioned to removably receive the outwardly extending arms 50 and 52 therein but allow pivotal movement of the lens structure 40 through an arc of substantially 90 degrees or until the transverse arms 50 and 52 are rotated to be received in the next adjacent sockets 56.

Another embodiment of the positioning means is shown in FIGS. 9, 10 and 11 wherein an outwardly extending finger 54 similar to the finger 54 in the embodiment of FIGS. 5, 6 and 8 extends outwardly from the exposed surface of the end 48. However, in this embodiment the transverse outwardly projecting members 52 and 54 are deleted and instead a single outwardly projecting nipple as at 75 is integrally formed. The nipple 75 extends in spaced relation to the finger 54 and is dimensioned to be received within one of two spaced apart apertures and/or sockets 78 and 80 integrally formed in the end portion 36 as clearly shown in FIG. 10. FIG. 11 shows that both the finger 54 and the nipple 75 project outwardly a sufficient degree to extend into the respective receiving aperture 58 explained with regard to the structure of FIG. 6 and also the two apertures 78 and 80 respectively. More specifically, rotation of the lens structure 40 from a covering relation as shown in FIG. 3 and an outwardly extending or shading position as shown in FIG. 4 is accomplished and maintained by changing the positioning of the nipples 75 from the aperture 78 and to the aperture 80.

At all times during positioning and rotational movement of the first member 49 relative to the transverse sockets 56, the outwardly extending finger is maintained substantially and at least in part within the receiving central aperture 58.

Therefore, the positioning means generally indicated in FIG. 1 as 58 allows for the selective positioning and removable maintenance of the lens structure 40 in either the viewing position as pictured in FIGS. 2, 3 and 7 or the shading position as pictured in FIG. 4. Other structural features particularly of the lens structure include side visors 60 which may be formed of a similar transparent, darkened or polarized material from which the lens portions 44 are formed, but which are arranged in substantially transverse relation thereto so as to cover the outer ends or corners of the eyes of the wearer thereby preventing any inadvertent light or glare from passing into the eyes from this outer position. The side visor 60 may be formed integral with the opposite ends 48 on the lens structure as clearly shown in FIGS. 3, 4, 5 and 7.

Now that the invention has been described,
What is claimed is:

1. A combination sun visor and sunglasses assembly designed to be worn on the head of a person, said assembly comprising:
   a. a mounting means structured for removable attachment in surrounding relation to a head of a wearer,
   b. a bracket structure secured to a front portion of the mounting means and disposed above the eyes of the wearer,
   c. a lens structure having an elongated configuration terminating at two opposite ends and formed of a darkened, transparent material and pivotally mounted on a leading portion of the bracket structure and selectively positionable between a viewing position and a shading position,
   d. said viewing position defined by substantially depending, transverse relation of said lens structure to said mounting means and an overlying disposition to the eyes of the wearer, whereby the wearer views through said lens structure,
   e. said shading position defined by an outwardly disposed substantially aligned and continuing extension of said lens structure with said mounting means, said shading position of said lens structure being disposed above and in shading relation to the eyes of the wearer,
   f. positioning means mounted in part on both said bracket structure and said lens structure and configured to removably maintain the lens structure in either said viewing position or said shading position, and
   g. said positioning means being disposed in part on each of said two opposite ends of said lens structure and in mating engagement with a remainder of said positioning means mounted on a correspondingly positioned opposite side of said bracket structure and in registry therewith.

2. An assembly as in claim 1 wherein said mounting means comprises a headband of adjustable length and disposable in surrounding relation to the head of the wearer.

3. An assembly as in claim 2 further comprising a sweatband structure including an elongated strip of moisture absorbent material removably secured to an inner surface of said headband.

4. An assembly as in claim 3 wherein said strip is of sufficient longitudinal dimension to extend along a frontal, inner surface of said headband in confronting engagement with the forehead surface area of the wearer.

5. An assembly as in claim 1 wherein said positioning means comprises a protruding member extending outwardly from each opposite end of said lens structure and a socket formed in each of said opposite sides of said bracket structure in removably, receiving relation to a corresponding protruding member.

6. An assembly as in claim 5 wherein said protruding member and said receiving socket are correspondingly configured to removably maintain said lens structure in either said viewing position or said shading position relative to said bracket and the eyes of the wearer.

7. An assembly as in claim 6 wherein each of said protruding members comprises two transversely intersecting arms and an outwardly projecting finger disposed perpendicular to the junction of said arm and extending outwardly from a common plane in which said arms are disposed.

8. An assembly as in claim 7 wherein said socket comprises two transversely disposed channels and a centrally disposed aperture, said aperture disposed at the junction of said channels; said channel and said aperture disposed and dimensioned to removably receive said arms and said finger respectively therein.

9. An assembly as in claim 8 wherein each of said ends of said lens structure is secured in transverse relation to a remaining portion of said lens structure and includes an inner surface disposed in overlapping, confronting engagement with an outer surface of respectively positioned ones of said opposite sides of said bracket structure.

10. An assembly as in claim 9 wherein said lens structure comprises an at least minimally greater longitudinal dimension than said front portion of said bracket structure, said opposite ends disposed in overlapping, biased, movable engagement with outer surfaces of opposite sides of said visor structure.

11. An assembly as in claim 1 wherein each of said opposite ends of said lens structure is secured in transverse relation to a remaining portion of said lens structure and includes an inner surface disposed in confronting engagement with an outer surface of respective ones of said opposite sides of said bracket structure.

12. An assembly as in claim 11 wherein said lens structure comprises an at least minimally greater longitudinal dimension than said front portion of said bracket structure, said opposite ends disposed in overlapping, biased, movable engagement with outer surfaces of said opposite sides of said bracket structure.

13. An assembly as in claim 6 wherein said protruding member comprises an outwardly extending nipple and an outwardly projecting finger each spaced from one another and extending outwardly from an inner surface of each opposite end of said lens structure, said lens structure pivotal about said finger relative to said bracket structure.

14. An assembly as in claim 13 wherein said socket comprises a finger receiving aperture and two nipple receiving apertures each formed in spaced relation to one another in a side of said bracket, said finger receiving aperture disposed in continuously and rotatably receiving relation to said finger and each of said nipple receiving apertures disposed to independently receive said nipple therein.

15. A combination sun visor and sunglasses assembly designed to be worn on the head of a person, said assembly comprising:

a. a mounting means structured for removable attachment in surrounding relation to a head of a wearer,
b. a bracket structure secured to a front portion of the mounting means and disposed above the eyes of the wearer,
c. a lens structure having an elongated configuration terminating at two opposite ends and formed of a darkened, transparent material and pivotally mounted on a leading portion of the bracket structure and selectively positionable between a viewing position and a shading position,
d. said viewing position defined by substantially depending, transverse relation of said lens structure to said mounting means and an overlying disposition to the eyes of the wearer, whereby the wearer views through said lens structure,
e. said shading position defined by an outwardly disposed substantially aligned and continuing extension of said lens structure with said mounting means, said shading position of said lens structure being disposed above and in shading relation to the eyes of the wearer,
f. positioning means mounted in part on both said bracket structure and said lens structure and configured to removably maintain the lens structure in either said viewing position or said shading position,
g. said positioning means being disposed in part on each of said two opposite ends of said lens structure and in mating engagement with a remainder of said positioning means mounted on a correspondingly positioned opposite side of said bracket structure and in registry therewith, and
h. a side visor mounted on each of said opposite ends of said lens structure and formed of a transparent, darkened material in transverse relation to a major portion of the length thereof in substantially covering relation to an outer end of a correspondingly positioned eye of the wearer when said lens structure is in said viewing position.

* * * * *